United States Patent
Zhang et al.

(10) Patent No.: US 9,579,033 B2
(45) Date of Patent: Feb. 28, 2017

(54) PAPER TRAY STRUCTURES AND ELECTROCARDIOGRAPH MACHINES

(71) Applicant: SHENZHEN MINDRAY BIO-MEDICAL ELECTRONICS CO., LTD., Shenzhen (CN)

(72) Inventors: Xuegang Zhang, Shenzhen (CN); Shen Luo, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 14/884,666

(22) Filed: Oct. 15, 2015

(65) Prior Publication Data
US 2016/0183820 A1  Jun. 30, 2016

Related U.S. Application Data

(63) Continuation-in-part of application No. PCT/CN2013/083108, filed on Sep. 9, 2013.

(51) Int. Cl.
*A61B 5/0402* (2006.01)
*A61B 5/0432* (2006.01)
*B65H 1/04* (2006.01)
*B65H 1/26* (2006.01)

(52) U.S. Cl.
CPC .......... *A61B 5/0402* (2013.01); *A61B 5/0432* (2013.01); *B65H 1/04* (2013.01); *B65H 1/26* (2013.01); *B65H 2405/12* (2013.01); *B65H 2407/20* (2013.01)

(58) Field of Classification Search
CPC ................................ A61B 5/0402; B65H 1/26
See application file for complete search history.

(56) References Cited

U.S. PATENT DOCUMENTS

| 2004/0230126 A1* | 11/2004 | Pingel | A61B 5/0402 600/509 |
| 2005/0258227 A1* | 11/2005 | Flores | A47G 29/1209 232/29 |
| 2006/0221168 A1* | 10/2006 | Wakiyama | B41J 13/106 347/108 |

(Continued)

FOREIGN PATENT DOCUMENTS

| CN | 101221383 A | 7/2008 |
| CN | 201320168 Y | 10/2009 |

(Continued)

*Primary Examiner* — Alessandro Amari
*Assistant Examiner* — Roger W Pisha, II
(74) *Attorney, Agent, or Firm* — Kory D. Christensen; Stoel Rives LLP

(57) ABSTRACT

This disclosure relates generally to medical devices, particularly to drawer-type paper tray structures for loading paper into electrocardiograph machines. A paper tray structure provided comprises a paper tray and a door component. The door component comprises a door located in front of the paper tray. The door component is connected to the paper tray movably and is configured to move repeatedly between a first position and a second position relative to the paper tray; the paper tray comprises a first restriction surface and a second restriction surface corresponding to the first and second positions respectively.

8 Claims, 6 Drawing Sheets

(56) References Cited

U.S. PATENT DOCUMENTS

| | | | | |
|---|---|---|---|---|
| 2008/0008516 A1* | 1/2008 | Bryant | ....................... | B41J 3/36 400/625 |
| 2009/0206545 A1 | 8/2009 | Sunohara | | |
| 2011/0210166 A1* | 9/2011 | Dinh | .................. | A47G 29/1209 232/17 |
| 2013/0044174 A1* | 2/2013 | Takemura | ................ | B41J 29/13 347/108 |

FOREIGN PATENT DOCUMENTS

| | | |
|---|---|---|
| CN | 202540958 U | 11/2012 |
| JP | 08217271 A | 8/1996 |
| JP | 2002273976 A | 9/2002 |

\* cited by examiner

PAPER TRAY STRUCTURES AND ELECTROCARDIOGRAPH MACHINES

FIELD OF THE INVENTION

The present disclosure relates generally to medical devices, particularly to drawer-type paper tray structures for loading paper into electrocardiograph machines.

BACKGROUND OF THE INVENTION

Conventional paper trays used in standard 12-lead ECG (electrocardiograph) machines are generally of two types. The first is a stationary type, where the paper tray structure is a closed chamber within the recorder. A4 paper or letter paper is loaded into the paper tray from the door of the paper tray after the door is opened. The paper tray in such arrangement occupies a small space inside the ECG machine, but it is inconvenient for a user to load paper. The second is a drawer type, where the paper tray and the door are fixed and are one unit. When the door is opened, the paper tray is drawn out simultaneously. This is more convenient for loading paper, but the paper tray in such arrangement occupies a larger space inside the ECG machine, so the machine must be wider. A wider ECG machine is usually set on a trolley, but it is not conducive for printing reports and is not convenient for viewing the printed waveform. Many ECG machines sold in the market have drawer-type paper trays. When using A4 paper for printing, the width of the ECG machine must be over 400 millimeters, which makes it inconvenient to use.

Thus, conventional paper trays for 12-lead ECG machines sold in the market have two disadvantages: (1) when a stationary-type paper tray is used, it is difficult to load paper; and (2) when a drawer-type paper tray is used, the ECG machine must be wider, making it less convenient to use.

SUMMARY OF THE INVENTION

In one embodiment, a paper tray structure provided according to an embodiment of the present disclosure comprises a paper tray with an operation space and a door component. The door component door component comprises a door located in front of the paper tray. The door component is connected to the paper tray movably and configured to move repeatedly between a first position and a second position relative to the paper tray. The paper tray comprises a first restriction surface and a second restriction surface corresponding to the first and second positions respectively. At the first position, the door component engages with the first restriction surface and disengages from the second restriction surface, allowing the operation space to open. At the second position, the door component disengages from the first restriction surface and engages with the second restriction surface, blocking the operation space.

In one embodiment, the door component and the paper tray cooperate with each other during their linear movement, and the door component is configured to move linearly and repeatedly between the first and second positions relative to the paper tray.

In one embodiment, the door component includes a platen roller. The platen roller is fixed to the door and suspended above the paper tray. The platen roller and the door both allow the operation space to be open at the first position, and at least one of the platen roller and the door blocks the operation space at the second position.

In one embodiment, the door component includes two linear guide rails parallel to each other. The door is fixed to the front of each linear guide rail respectively, the paper tray is located between the two linear guide rails, and the platen roller is perpendicular to both linear guide rails.

In one embodiment, the door component includes a first restriction member and a second restriction member, and both the first and second restriction surfaces are located between the first and second restriction members. At the first position, the first restriction member engages with the first restriction surface and the second restriction member disengages from the second restriction surface, At the second position, the first restriction member disengages from the first restriction surface and the second restriction member engages with the second restriction surface.

In one embodiment, the first restriction member is located on both linear guide rails; the second restriction member is located on the door; the first restriction surface is located in the middle of the paper tray; and the second restriction surface is located on the front of the paper tray.

In one embodiment, there may be only one restriction member, and it can be located between the first and second restriction surfaces.

The paper tray can include of a plurality of blocking plates, and both the first and the second restriction surfaces can be located on side blocking plates. Alternately, one of the restriction surfaces could be located on the side blocking plates of the paper tray, and another could be located on a front blocking plate of the paper tray.

In another embodiment, an ECG machine is used, which includes a host and a paper tray structure like those described above. Both the door component and the paper tray are linearly movable relative to the host. When the door component of the paper tray structure is opened, the door component is located at the first position relative to the paper tray and the paper tray is pulled out of the host; when the door component of the paper tray is closed, the door component is located at the second position relative to the paper tray, and the paper tray is pushed back into the host.

In one embodiment, the door component and the paper tray cooperate with each other during their linear movement, and the door component is configured to move linearly and repeatedly between the first and second positions relative to the paper tray.

In one embodiment, the door component includes a platen roller. The platen roller is fixed to the door and suspended above the paper tray. The platen roller and the door both unblock the operation space at the first position, and at least one of the platen roller and the door blocks the operation space at the second position.

In one embodiment, the door component includes two linear guide rails parallel to each other. The door is fixed to the front of each linear guide rail respectively, the paper tray is located between the two linear guide rails, and the platen roller is perpendicular to both the linear guide rails.

In one embodiment, the door component includes a first restriction member and a second restriction member, and both the first and second restriction surfaces are located between the first and second restriction members. At the first position, the first restriction member engages with the first restriction surface and the second restriction member disengages from the second restriction surface. At the second position, the first restriction member disengages from the first restriction surface and the second restriction member engages with the second restriction surface.

In one embodiment, the first restriction member is located on both linear guide rails; the second restriction member is located on the door; the first restriction surface is located in the middle of the paper tray; and the second restriction surface is located on the front of the paper tray.

According to the paper tray structure and ECG machine of the present disclosure, the door component could move repeatedly relative to the paper tray, allowing the ECG machine to be smaller and making it more convenient to load paper.

DETAILED DESCRIPTION OF THE EMBODIMENTS

Figure 1:
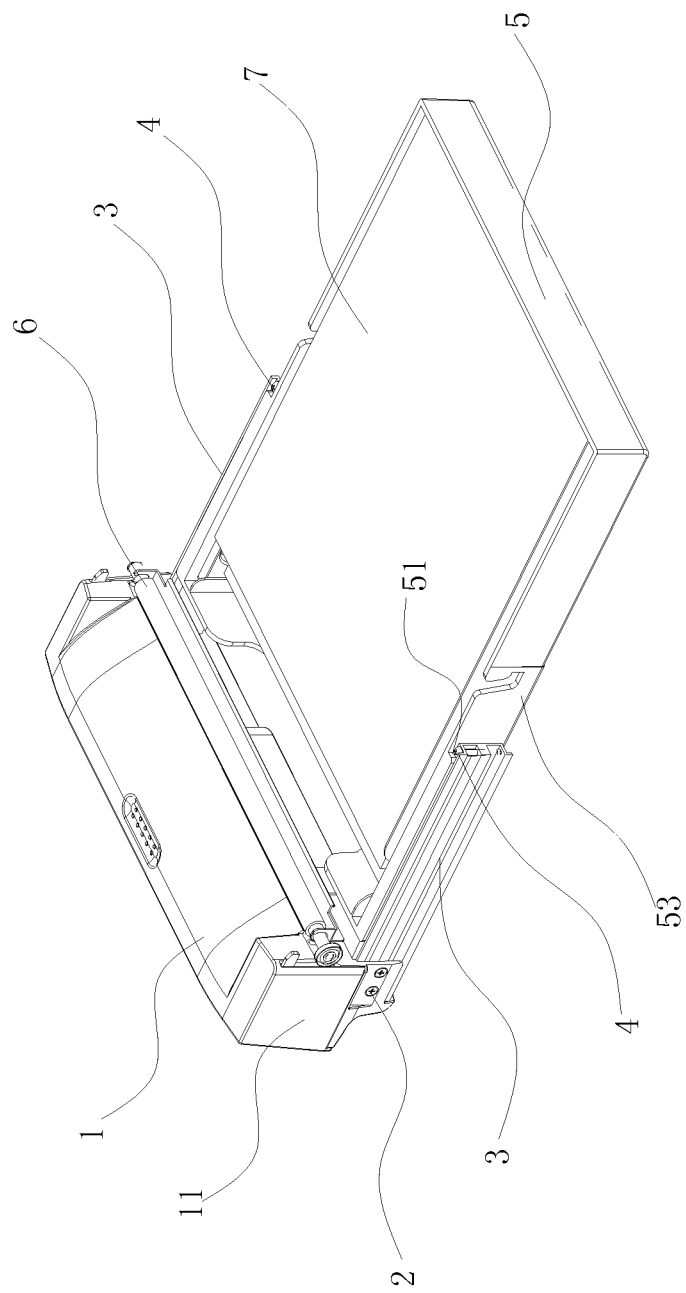
FIG. 1 shows a perspective view of a paper tray.

Referring to FIG. 1 through FIG. 6, in one embodiment, a paper tray structure includes a paper tray 5 and a door component 11 thereabove. The paper tray 5 is configured to hold paper. Users could load paper into the paper tray 5 via an operation space which is provided above the paper tray 5. The door component 11, which could move linearly and repeatedly, includes a door 1. When the door 1 is opened, the door component 11 could be drawn out with the paper tray 5 simultaneously. When the door 1 is closed, the door component 11 could be drawn inside with the paper tray 5 simultaneously. The door component 11 is movably connected to the paper tray 5, thus enabling the door component 11 to move repeatedly between a first position and a second position; that is, the door component 11 could not only drive the paper tray 5 to move simultaneously but could also move independently relative to the paper tray 5. The reciprocating movement is a linear reciprocating movement.

The paper tray 5 includes a first restriction surface 51 and a second restriction surface 52, which are corresponding to the first position and the second position respectively. When reaching the first position, the door component 11 engages with the first restriction surface 51 and disengages from the second restriction surface 52. The term "engage" means that the two elements contact each other under a force; the term "disengage" means the two elements are separate from each other and release the contact. When the door 1 continues to move along a same direction, the door component 11 could pull the paper tray 5 out simultaneously. When reaching the second position, the door component 11 engages with the second restriction surface 52 and disengages from the first restriction surface 51. When the door 1 continues to move along a same direction, the door component 11 could push the paper tray 5 back simultaneously. In an initial state, the door component 11 is located at the second position relative to the paper tray 5.

At the first position, the door component 11 allows the operation space to open above the paper tray 5, to allow a user to load paper into the paper tray 5. In the second position, the door component 11 blocks the operation space above the paper tray 5, or blocks at least part of the operation space above the front of the paper tray 5.

The paper tray 5 is movably connected to the door component 11, so a two-stage movement could be achieved during opening or closing of the door component 11. During the first stage movement, the paper tray 5 does not move, and the door component 11 moves relative to the paper tray 5. During the second stage movement, the door component 11 moves with the paper tray 5 simultaneously.

Referring to FIG. 1 through FIG. 6, in an alternative embodiment, the paper tray structure could be used in an ECG machine. The paper tray structure includes a door component 11 and a paper tray 5. The door component 11 could move linearly and repeatedly, and it includes two linear guide rails 3, a door 1, a thermal printing head platen roller 6, and two stopper pins 4. The two linear guide rails 3 are parallel to each other and arranged along a moving direction of the door component 11. The door 1 is located in front of the two linear guide rails 3 via a fastener 2. The platen roller 6 presses the paper and is fixed to the door 1. The platen roller 6 is perpendicular to the two linear guide rails 3. Each stopper pin 4 is fixed to a rear of each linear guide rail 3 respectively. The paper tray 5 is movably connected to the door component 11 via the stopper pins 4, such that the door component 11 could move repeatedly between the first position and the second position relative to the paper tray 5. The paper tray 5 includes a first restriction surface 51 located in the middle of the paper tray 5 and a second restriction surface 52 on the front of the paper tray 5. The first restriction surface 51 could be located in the middle of a side blocking plate of the paper tray 5, and the second restriction surface 52 could be located on a front blocking plate of the paper tray 5 or on the front of a bottom plate 54.

Figure 2:
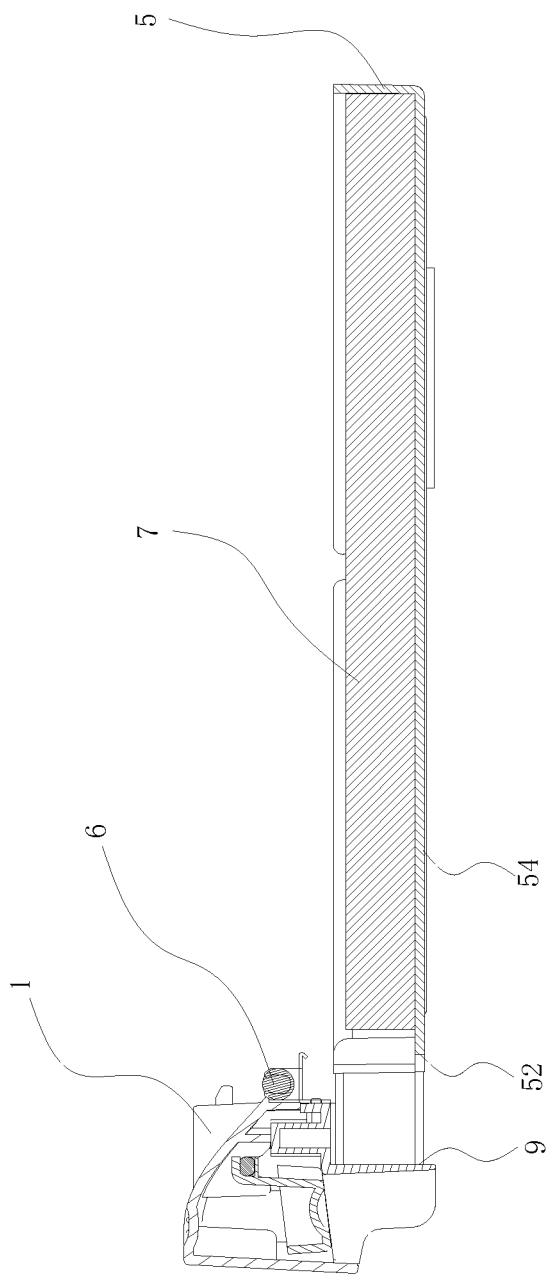
FIG. 2 shows a cross-sectional view of a paper tray structure.
Figure 3:
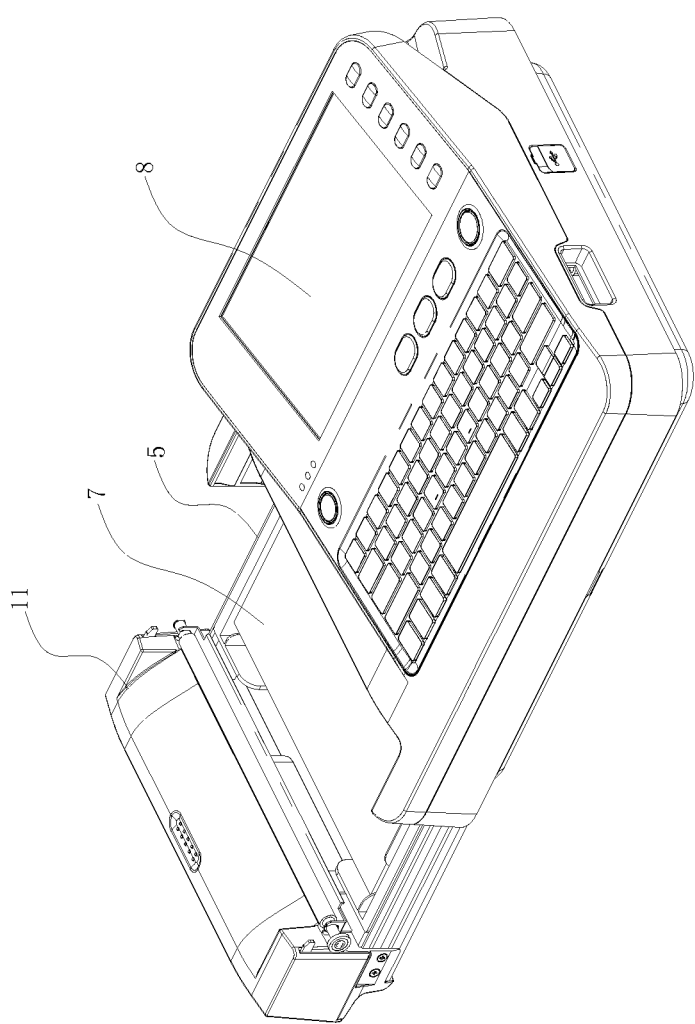
FIG. 3 shows a perspective view of an ECG machine.

Referring to FIG. 1 through FIG. 3, when a user opens the door component 11, the door component 11 moves relative to an ECG machine host 8 for a first distance; the distance is determined by the relative distance between the linear guide rail 3 and the paper tray 5. After the door component 11 reaches a first position (that is, the door component 11 moves relative to the paper tray 5 to the first position), the stopper pins 4 resist the first restriction surface 51, resulting in forced contact between the door component 11 and the paper tray 5. Then, the paper tray 5 is pulled by the stopper pins 4 of the linear guide rails 3 to move a distance from the ECG machine host 8 (that is, the paper tray 5 is pulled out of the host 8). At this time, the door 1 of the door component 11 and the platen roller 6 allow the operation space to open above a thermal sensitive paper 7 in the paper tray 5, thus making it convenient to load paper.

Figure 4:
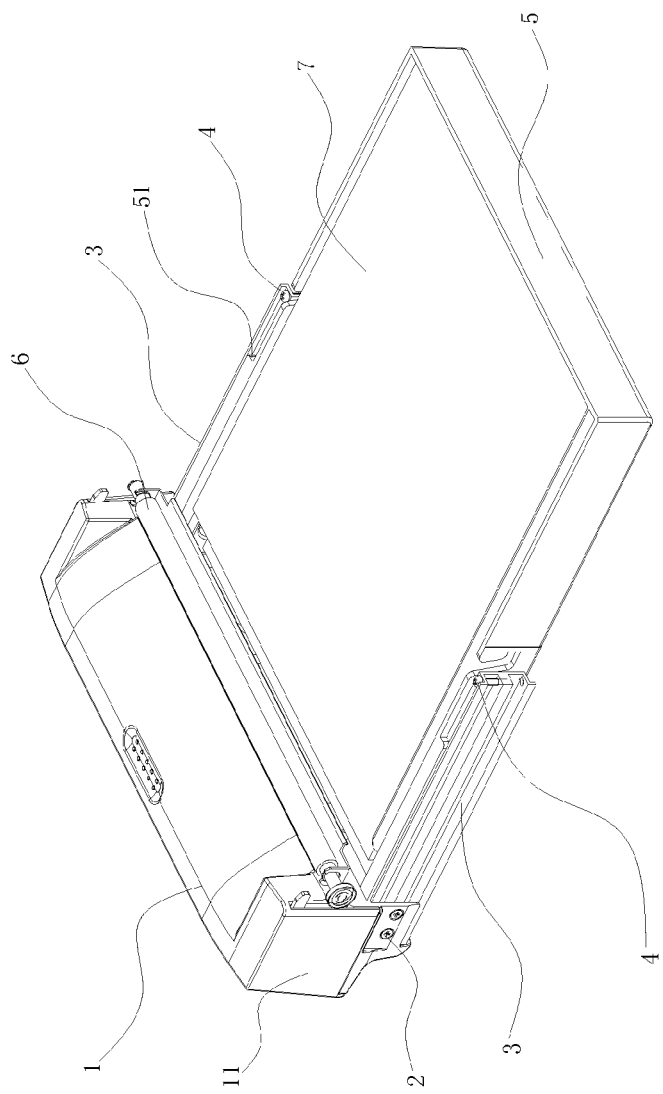
FIG. 4 shows a perspective view of a paper tray structure.
Figure 5:
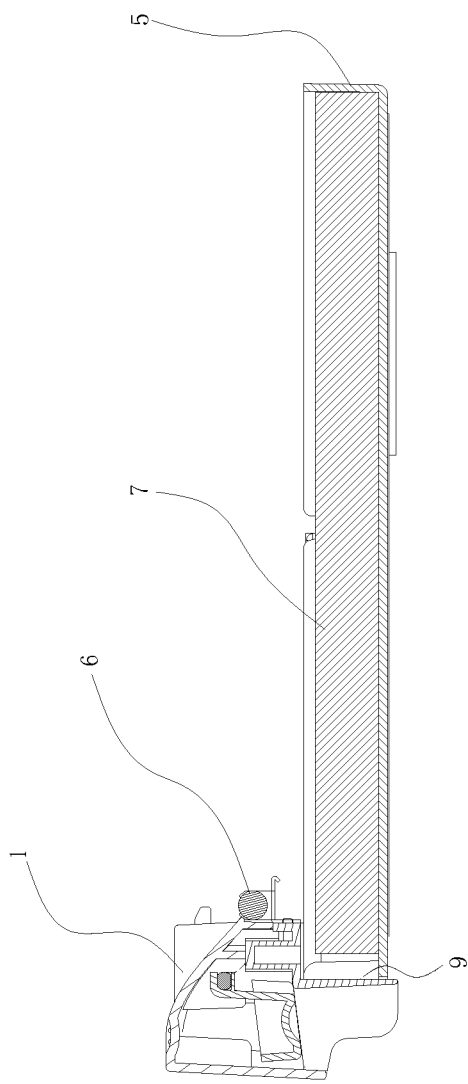
FIG. 5 shows a cross-sectional view of a paper tray structure.
Figure 6:
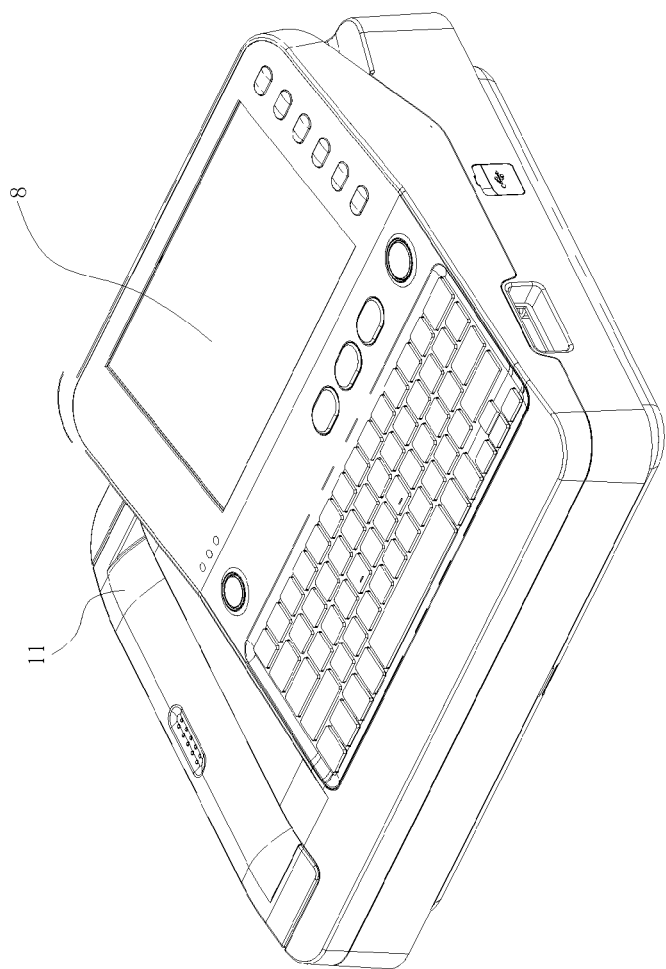
FIG. 6 shows a perspective view of an ECG machine.

Referring to FIG. 4 through FIG. 6, after loading the paper, and during the closing of the door component 11, the door component 11 moves relative to the paper tray 5 for a distance. After the door component 11 reaches a second position (that is, the door component 11 moves relative to the paper tray 5 and reaches the second position), the paper tray 5 is drawn back into the ECG machine host 8 by the door component 11. At this time, the door 1 of the door component 11 and the platen roller 6 block the operation space above the thermal sensitive paper 7 in the paper tray 5.

In the illustrated embodiment, the door component 11 includes a first restriction member and a second restriction member corresponding to the first restriction surface 51 and the second restriction surface 52 respectively. The first restriction member is the stopper pins 4. The second restriction member 9 is located on the door 1. For example, the second restriction member 9 could be an end surface of the door 1 facing the paper tray 5.

The paper tray structure includes a door component and a paper tray. The door component is movably connected to the paper tray, so the door component could move linearly and repeatedly relative to the paper tray. The paper tray includes a first restriction surface and a second restriction surface to restrict the relative moving distance between the paper tray and the door component. When the door component is opened, the door component engages with the first restriction surface and disengages from the second restriction surface. When the door component is closed, the door component engages with the second restriction surface and disengages from the first restriction surface. Both the first and second restriction surfaces could be located on the side blocking plates of the paper tray. The side blocking plate coordinates with the linear guide rails of the door component. In this embodiment, there can be only one restriction member of the door component, and the restriction member moves repeatedly between the first and second restriction surfaces. Alternatively, the first restriction surface could be located on the side blocking plate of the paper tray, and the second restriction surface could be located on the front blocking plate of the paper tray or on the front of the bottom plate of the paper tray. In this embodiment, the linear guide rails and the door are both provided with restriction bodies, and the first and second restriction surfaces are located between the two restriction bodies.

The paper tray structure could be applied to the ECG machine that includes a host. When the door component is opened, the door component is located at the first position relative to the paper tray, and the paper tray is pulled out of the host. When the door component is closed, the door component is located at the second position relative to the paper tray, and the paper tray is pushed back into the host. The door component coordinates with the host by a linear movement, e.g., the linear guide rails could coordinate with the host by a linear movement. Alternatively, the paper tray can directly coordinate with the host by a linear movement or can indirectly coordinate with the host by a linear movement via the door component.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A paper tray structure, comprising:
a paper tray with an operation space there above; and
a door component comprising a door located in front of the paper tray;
wherein the door component is connected to the paper tray movably and the door component is configured to move repeatedly between a first position and a second position relative to the paper tray; the paper tray comprises a first restriction surface and a second restriction surface corresponding to the first and second positions respectively; at the first position, the door component engages with the first restriction surface and disengages with the second restriction surface, and the door component lets the operation space open; at the second position, the door component disengages with the first restriction surface and engages with the second restriction surface, and the door component blocks the operation space;
wherein the door component and the paper tray cooperate with each other during their linear movement, and the door component is configured to move linearly and repeatedly between the first and second positions relative to the paper tray;
wherein the door component comprises a platen roller; the platen roller is fixed to the door and suspended above the paper tray; the platen roller and the door both let the operation space open at the first position; and at least one of the platen roller and the door blocks the operation space at the second position.

2. The paper tray structure according to claim 1, wherein the door component comprises two linear guide rails parallel to each other, the door is fixed to a front part of each linear guide rail respectively, the paper tray is located between the two linear guide rails, and the platen roller is perpendicular to both liner guide rails.

3. The paper tray structure according to claim 2, wherein the door component comprises a first restriction member and a second restriction member, both the first and second restriction surfaces are located between the first and second restriction members; at the first position, the first restriction member engages with the first restriction surface and the second restriction member disengages with the second restriction surface; at the second position, the first restriction member disengages with the first restriction surface and the second restriction member engages with the second restriction surface.

4. The paper tray structure according to claim 3, wherein the first restriction member is located on both linear guide rails, the second restriction member is located on the door, the first restriction surface is located on a middle part of the paper tray, and the second restriction surface is located on a front part of the paper tray.

5. An ECG (electrocardiograph) machine, comprising:
a host, and
a paper tray;
wherein the paper tray comprises a paper tray with an operation space there above and a door component comprising a door located in front of the paper tray;
wherein the door component is connected to the paper tray movably and the door component is configured to move repeatedly between a first position and a second position relative to the paper tray; the paper tray comprises a first restriction surface and a second restriction surface corresponding to the first and second positions respectively; at the first position, the door component engages with the first restriction surface and disengages with the second restriction surface, and the door component lets the operation space open; at the second position, the door component disengages with the first restriction surface and engages with the second restriction surface, and the door component blocks the operation space;
wherein both the door component and the paper tray are linearly movable relative to the host; when the door component of the paper tray structure is opened, the door component is located at the first position relative to the paper tray and the paper tray is pulled out of the host; when the door component of the paper tray is closed, the door component is located at the second position relative to the paper tray, and the paper tray is push back into the host;
wherein the door component and the paper tray cooperates with each other during their linear movement, and the door component is configured to move linearly and repeatedly between the first and second positions relative to the paper tray;
wherein the door component comprises a platen roller; the platen roller is fixed to the door and suspended above the paper tray; the platen roller and the door let unblock the operation space open at the first position; and at least one of the platen roller and the door blocks the operation space at the second position.

6. The ECG (electrocardiograph) machine according to claim 5, wherein the door component comprises two linear guide rails parallel to each other, the door is fixed to a front part of each linear guide rail respectively, the paper tray is located between the two linear guide rails, and the platen roller is perpendicular to both the liner guide rails.

7. The ECG (electrocardiograph) machine according to claim 6, wherein the door component comprises a first restriction member and a second restriction member, both the first and second restriction surfaces are located between the first and second restriction members; at the first position, the first restriction member engages with the first restriction surface and the second restriction member disengages with the second restriction surface; at the second position, the first restriction member disengages with the first restriction surface and the second restriction member engages with the second restriction surface.

8. The ECG (electrocardiograph) machine according to claim 7, wherein the first restriction member is located on both linear guide rails, the second restriction member is located on the door, the first restriction surface is located on a middle part of the paper tray, and the second restriction surface is located on a front part of the paper tray.

* * * * *